US00PP32845P3

(12) United States Plant Patent
Koot

(10) Patent No.: US PP32,845 P3
(45) Date of Patent: Feb. 23, 2021

(54) ***DELOSPERMA* PLANT NAMED 'DODELROCHRYOR'**

(50) Latin Name: *Delosperma cooperi*
Varietal Denomination: Dodelrochryor

(71) Applicant: DUMMEN GROUP B.V., De Lier (NL)

(72) Inventor: Arjan Koot, Oeffelt (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 16/873,424

(22) Filed: Apr. 9, 2020

(65) Prior Publication Data

US 2020/0329616 P1 Oct. 15, 2020

(51) Int. Cl.
*A01H 5/02* (2018.01)
*A01H 6/00* (2018.01)

(52) U.S. Cl.
USPC ..... Plt./422
CPC ..... *A01H 6/00* (2018.05)

(58) Field of Classification Search
USPC ..... Plt./422
CPC ..... A01H 5/02
See application file for complete search history.

(56) References Cited

PUBLICATIONS

PLUTO UPOVROM Plant Variety Database Citation for 'Dodelrochryor' as per QZ PBR 20192801; Feb. 16, 2020; 1 page.*

* cited by examiner

*Primary Examiner* — Kent L Bell
(74) *Attorney, Agent, or Firm* — C. A. Whealy

(57) ABSTRACT

A new and distinct cultivar of *Delosperma* plant named 'Dodelrochryor', characterized by its upright and outwardly spreading plant habit; typically used as a groundcover; moderately vigorous growth habit and rapid growth rate; freely basal branching habit; dense and bushy habit; early and freely flowering habit; large bright orange red-colored flowers with white and light purple-colored centers; and good garden performance.

2 Drawing Sheets

Figure 1:
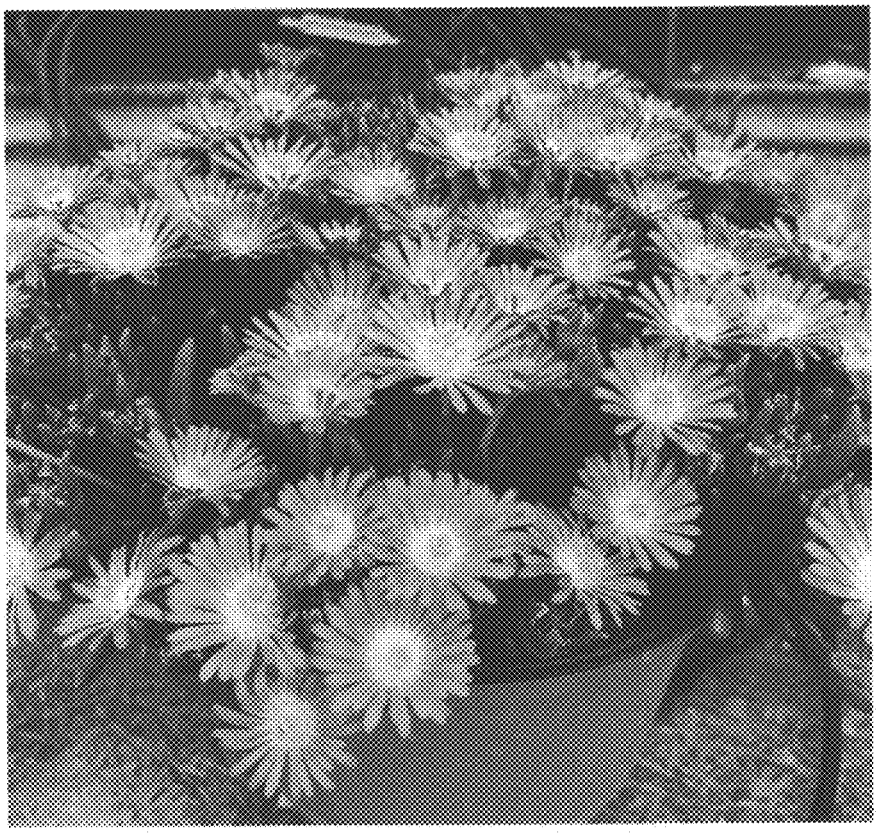

Botanical designation: *Delosperma cooperi.*
Cultivar denomination: 'DODELROCHRYOR'.

STATEMENT REGARDING PRIOR DISCLOSURES BY THE APPLICANT

The Applicant asserts that no publications nor advertisements relating to sales, offers for sale or public distribution occurred more than one year prior to the effective filing date of this application. Any information about the claimed plant would have been obtained from a direct or indirect disclosure from the Inventor. Applicant claims a prior art exemption under 35 U.S.C. 102(b)(1) for disclosure and/or sales prior to the filing date but less than one year prior to the effective filing date. Disclosures include a reference to the claimed plant on the website of Dümmen Orange B.V.

BACKGROUND OF THE INVENTION

The present invention relates to a new and distinct cultivar of *Delosperma* plant, botanically known as *Delosperma cooperi*, commonly called Trailing Ice Plant and hereinafter referred to by the name 'Dodelrochryor'.

The new *Delosperma* plant is a product of a planned breeding program conducted by the Inventor in Rheinberg, Germany. The objective of the breeding program is to create new early-flowering *Delosperma* plants with numerous attractive flowers.

The new *Delosperma* plant originated from a self-pollination in July, 2016 of a proprietary selection of *Delosperma*

*cooperi* identified as code number DL-0006, not patented. The new *Delosperma* plant was discovered and selected by the Inventor as a single flowering plant from within the progeny of the stated self-pollination in a controlled environment in Rheinberg, Germany in May, 2019.

Asexual reproduction of the new *Delosperma* plant by vegetative terminal cuttings in Rheinberg, Germany, since June, 2019 has shown that the unique features of this new *Delosperma* plant are stable and reproduced true to type in successive generations.

SUMMARY OF THE INVENTION

Plants of the new *Delosperma* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Dodelrochryor'. These characteristics in combination distinguish 'Dodelrochryor' as a new and distinct *Delosperma* plant:

1. Upright and outwardly spreading plant habit; typically used as a groundcover.
2. Moderately vigorous growth habit and rapid growth rate.
3. Freely basal branching habit; dense and bushy habit.
4. Early and freely flowering habit.

5. Large bright orange red-colored flowers with white and light purple-colored centers.
6. Good garden performance.

Plants of the new *Delosperma* differ primarily from plants of the parent selection in flower color as plants of the new *Delosperma* have bright orange red-colored flowers with white and light purple-colored centers whereas plants ofthe parent selection have pink-colored flowers.

Plants of the new *Delosperma* can be compared to plants of *Delosperma cooperi* 'Dodelrochrypu', disclosed in U.S. Plant patent application 16/873,422 filed concurrently. Plants of the new *Delosperma* differ primarily from plants of 'Dodelrochrypu' in flower color as plants of the new *Delosperma* have bright orange red-colored flowers with white and light purple-colored centers whereas plants of 'Dodelrochrypu' have purple-colored flowers with white-colored centers.

Plants of the new *Delosperma* can also be compared to plants of *Delosperma cooperi* 'Jewels of Desert Topaz', disclosed in U.S. Plant Pat. No. 23,492. In side-by-side comparisons, plants of the new *Delosperma* differ from plants of 'Jewels of Desert Topaz' in the following characteristics:

1. Plants of the new *Delosperma* are more compact than plants of 'Jewels of Desert Topaz'.
2. Plants of the new *Delosperma* have shorter leaves than plants of 'Jewels of Desert Topaz'.
3. Plants of the new *Delosperma* have bright orange red-colored flowers with white and light purple-colored centers whereas plants of 'Jewels of Desert Topaz' have yellow orange-colored flowers with red-colored petal apices.
4. Plants of the new *Delosperma* have shorter peduncles than plants of 'Jewels of Desert Topaz'.

BRIEF DESCRIPTION OF THE PHOTOGRAPHS

The accompanying colored photographs illustrate the overall appearance of the new *Delosperma* plant showing the colors as true as it is reasonably possible to obtain in colored reproductions of this type. Colors in the photographs may differ slightly from the color values cited in the detailed botanical description which accurately describe the colors of the new *Delosperma* plant.

The photograph on the first sheet (FIG. 1 of 2) is a side perspective view of a typical flowering plant of 'Dodelrochryor' grown in a container.

Figure 2:
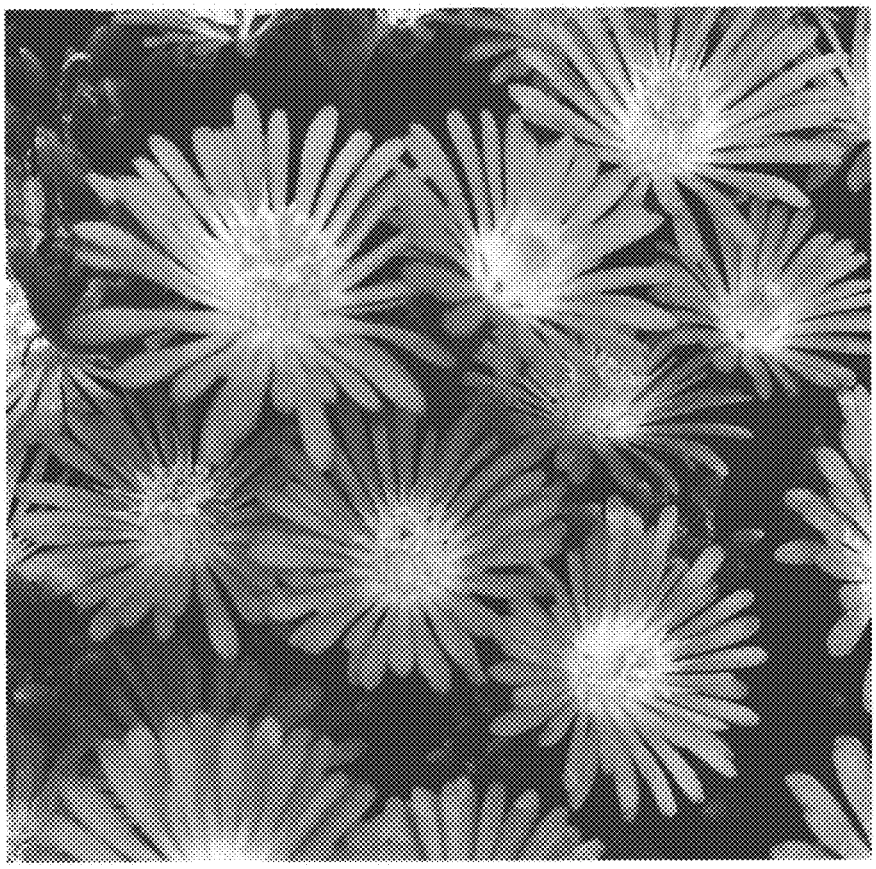

The photograph on the second sheet (FIG. 2 of 2) is a close-up view of a typical flowering plant of 'Dodelrochryor'.

DETAILED BOTANICAL DESCRIPTION

The aforementioned photographs and following observations and measurements describe plants grown in 22-cm containers during the spring in a glass-covered greenhouse in Rheinberg, Germany and under cultural practices typical of commercial *Delosperma* production. During the production of the plants, day and night temperatures averaged 18° C. and light levels averaged 4,500 lux. Plants were pinched once three weeks after planting and were three months old when the photographs and description were taken. In the following description, color references are made to The Royal Horticultural Society Colour Chart, Fifth Edition, except where general terms of ordinary dictionary significance are used.

Botanical classification: *Delosperma cooperi* 'Dodelrochryor'.

Parentage:

*Female, or seed, parent.*—Proprietary selection of *Delosperma cooperi* identified as code number DL-0006, not patented.

*Male, or pollen, parent.*—Proprietary selection of *Delosperma cooperi* identified as code number DL-0006, not patented.

Propagation:

*Type.*—Terminal vegetative cuttings.

*Time to initiate roots, summer.*—About five days at temperatures about 20° C.

*Time to initiate roots, winter.*—About one week at temperatures about 20° C.

*Time to produce a rooted young plant, summer.*—About three weeks at temperatures about 20° C.

*Time to produce a rooted young plant, winter.*—About four weeks at temperatures about 20° C.

*Root description.*—Fine, fibrous; typically white, close to 155D, in color, actual color of the roots is dependent on substrate composition, water quality, fertilizer type and formulation, substrate temperature and physiological age of roots.

*Rooting habit.*—Freely branching, medium density.

Plant description:

*Plant and growth habit.*—Herbaceous perennial grown as a container and landscape plant and typically used as a groundcover; upright and outwardly spreading plant habit; freely flowering habit with numerous flowers positioned above the foliar plane; appropriate for 9 to 22-cm containers; moderately vigorous growth habit and rapid growth rate.

*Plant height.*—About 4 cm.

*Plant diameter.*—About 28 cm.

*Branching habit.*—Freely branching habit with about three primary lateral branches each with about six secondary lateral branches developing per plant; pinching (removal of the terminal apex) enhances lateral branch development.

Lateral branch description:

*Length.*—About 7 cm.

*Diameter.*—About 3 mm.

*Internode length.*—About 1.5 cm.

*Strength.*—Relatively weak.

*Texture and luster.*—Moderately pubescent; semi-glossy.

*Color, developing.*—Close to 145A.

*Color, developed.*—Close to 146D; at the internodes, close to 142C.

Leaf description:

*Arrangement.*—Decussate, simple; sessile.

*Length.*—About 2.7 cm.

*Width.*—About 4 mm.

*Shape.*—Ligulate, triangular in cross-section.

*Apex.*—Acute.

*Base.*—Cuneate.

*Margin.*—Entire, not undulate.

*Texture and luster, upper and lower surfaces.*—Moderately pubescent; semi-glossy; succulent.

*Venation pattern.*—Pinnate.

*Color.*—Developing leaves, upper and lower surfaces: Close to 143A. Fully developed leaves, upper and lower surfaces: Close to 143A; venation, close to 143A.

Flower description:

*Flower arrangement and habit.*—Single rotate terminal flowers; freely flowering habit with about 178 flowers developing per plant during the flowering season; flowers face upright to outwardly.

*Fragrance.*—Faint, sweet and pleasant.

*Natural flowering season.*—Plants of the new *Delosperma* begin flowering about eight weeks after planting and flower from June to September in the landscape in Germany.

*Flower longevity.*—Flower last about five to six days; flowers not persistent.

*Flower diameter.*—About 1.7 cm.

*Flower length* (*height*).—About 7 mm.

*Flower buds.*—Length: About 8 mm. Diameter: About 4 mm. Shape: Ovate to oblong. Texture and luster: Moderately pubescent; semi-glossy. Color: Close to 144A.

*Petals.*—Arrangement: About 33 petals in about two whorls. Length: About 7 mm. Width: About 1 mm. Shape: Oblanceolate. Apex: Obtuse. Base: Truncate. Margin: Entire, not undulate. Texture and luster, upper and lower surfaces: Smooth, glabrous; glossy. Color: When opening and fully opened, upper surface: Close to 33B; towards the base, 75B and at the base, close to 155C; venation, similar to lamina; colors becoming closer to 46A, 63B and 155C with development. When opening and fully opened, lower surface: Close to 46A; towards the base, close to 63B; venation, similar to lamina; colors do not change with development.

*Petaloids.*—Arrangement: About 30 petaloids in about two whorls. Length: About 5 mm. Width: About 0.5 mm. Shape: Lanceolate. Apex: Acute. Base: Truncate. Margin: Entire, not undulate. Texture and luster, upper and lower surfaces: Smooth, glabrous; glossy. Color: When opening, upper and lower surfaces: Close to 75B. Fully opened, upper and lower surfaces: Close to 75B; towards the apex, close to 33B; venation, similar to lamina; color does not change with development.

*Sepals.*—Appearance: Five in a single whorl forming a star-shaped calyx; about 6 mm in height and about 5 mm in diameter. Length: About 6 mm. Width: About 2 mm. Shape: Ovate. Apex: Acute. Base: Cuneate. Margin: Entire. Texture and luster, upper and lower surfaces: Smooth; glabrous; semi-glossy. Color: When opening and fully opened, upper surface: Close to 146A. When opening and fully opened, lower surface: Close to 146A.

*Peduncles.*—Length: About 1.7 cm. Diameter: About 2 mm. Strength: Relatively weak. Texture and luster: Moderately pubescent; semi-glossy. Color: Close to 146D.

*Reproductive organs.*—Androecium: Stamen number: About 65 per flower. Filament length: About 3 mm. Filament color: Close to 155C. Anther length: About 1 mm. Anther shape: Ellipsoidal. Anther color: Close to 13C. Amount of pollen: Moderate. Pollen color: Close to 3A. Gynoecium: Pistil number: About five. Pistil length: About 2 mm. Style length: About 1 mm. Style color: Close to 22A. Stigma diameter: About 1 mm. Stigma shape: Triangular, lobed. Stigma color: Close to 22A. Ovary color: Close to 143D.

*Fruits.*—Quantity: About 190 fruits develop per plant. Length: About 1 cm. Diameter: About 9 mm. Texture: Moderately pubescent. Color: Close to 161A.

*Seeds.*—Quantity: About 146 seeds develop per fruit. Length: About 1 mm. Diameter: About 1 mm. Texture: Rough, knobby. Color: Close to 166C.

Garden performance: Plants of the new *Delosperma* have been observed to have good garden performance and to tolerate temperatures from about 5° C. to about 40° C.

Pathogen & pest resistance: To date, plants of the new *Delosperma* have not been observed to be resistant to pathogens and pests common to *Delosperma* plants.

It is claimed:

1. A new and distinct *Delosperma* plant named 'Dodelrochryor' as illustrated and described.

* * * * *